United States Patent [19]

Baugh et al.

[11] Patent Number: 4,533,519

[45] Date of Patent: Aug. 6, 1985

[54] GAS FLOW COAGULATION TEST CARTRIDGE HAVING MOVABLE MEMBER ESTABLISHING COMMUNICATION BETWEEN REAGENT AND REACTION CHAMBERS

[75] Inventors: Robert F. Baugh, Aurora; Walter J. Braun, Englewood; Daniel Cooper, Parker, all of Colo.

[73] Assignee: HemoTec, Inc., Englewood, Colo.

[21] Appl. No.: 515,914

[22] Filed: Jul. 20, 1983

[51] Int. Cl.³ .......................................... G01N 33/16
[52] U.S. Cl. ..................................... 422/73; 73/64.1;
356/39; 422/103; 422/58; 422/61; 422/102; 436/69
[58] Field of Search ................ 422/57, 58, 61, 73, 422/100–103, 119, 46, 47; 436/69, 165, 809; 73/57, 64.1; 435/13; 256/39; 210/918

[56] References Cited

U.S. PATENT DOCUMENTS

| | | | |
|---|---|---|---|
| 2,129,043 | 9/1938 | Bortsch | 73/57 |
| 3,038,327 | 6/1962 | Resnick | 73/64.1 |
| 3,077,106 | 2/1963 | Fink | 73/64.1 |
| 3,307,392 | 3/1967 | Owen et al. | 73/64.1 |
| 3,450,501 | 6/1969 | Oberhardt | 422/73 |
| 3,492,096 | 1/1970 | Hattersley | 436/69 |
| 3,525,254 | 8/1970 | Milanes | 73/64.1 |
| 3,560,162 | 2/1971 | Mittleman | 422/73 |
| 3,560,163 | 2/1971 | Mittleman | 422/73 |
| 3,635,678 | 1/1972 | Seltz et al. | 436/69 |
| 3,658,480 | 4/1972 | Kane et al. | 436/69 |
| 3,692,487 | 9/1972 | Sanz | 422/61 |
| 3,695,842 | 10/1972 | Mintz | 436/150 |
| 3,704,099 | 11/1972 | Sanz | 422/73 |
| 3,713,780 | 1/1973 | Shapiro | 422/61 |
| 3,719,075 | 3/1973 | Mandrona et al. | 73/57 |
| 3,741,002 | 6/1973 | Simons | 73/64.1 |
| 3,814,585 | 6/1974 | Bailly | 436/69 |
| 3,854,324 | 12/1974 | Altshuler et al. | 73/64.1 |
| 3,911,728 | 10/1975 | Fixot | 73/55 |
| 3,918,908 | 11/1975 | Moyer et al. | 436/69 |
| 3,963,349 | 6/1976 | Albright et al. | 73/64.1 |
| 4,000,972 | 1/1977 | Braun et al. | 436/69 |
| 4,074,971 | 2/1978 | Braun et al. | 436/69 |
| 4,081,242 | 3/1978 | Girolami | 73/64.1 |
| 4,160,801 | 6/1979 | Badolato et al. | 422/46 |
| 4,210,623 | 6/1980 | Breno et al. | 422/101 |
| 4,362,698 | 12/1982 | Boosalis et al. | 422/102 |

Primary Examiner—Barry S. Richman
Assistant Examiner—Joseph P. Carrier
Attorney, Agent, or Firm—John R. Ley

[57] ABSTRACT

A gas flow cartridge in which to conduct a coagulation-related test uses an elongated pin member movably positioned within a communication opening which separates a reagent chamber from a reaction chamber. A first portion of the pin member has an operative configuration for sealing the communication opening when the first portion is positioned in the communication opening. A second longitudinally displaced portion of the pin member opens the communication opening to further communication therethrough upon longitudinal movement of the pin member. At the commencement of an analytical test, a plug member is moved upwardly to contact the pin member and move the first portion out of the communication opening and the second portion into the communication opening. The upward movement of the lower plug member forces the contents of the reagent chamber through the opened communication opening and into the reaction chamber. A pointed needle-like member pierces a membrane of the lower plug member and injects gas into the cartridge. The gas also flows through the opened communication opening.

22 Claims, 9 Drawing Figures

GAS FLOW COAGULATION TEST CARTRIDGE HAVING MOVABLE MEMBER ESTABLISHING COMMUNICATION BETWEEN REAGENT AND REACTION CHAMBERS

REFERENCE TO RELATED APPLICATION

This is related to Application Ser. No. 434,718 for "Coagulation Detection by Gas Flow or Plunger Sensing Techniques", filed Oct. 15, 1982 and assigned to the assignee of the present invention. The subject matter of said application is incorporated in this application by reference.

BACKGROUND OF THE INVENTION

This invention pertains to measuring and detecting coagulation and coagulation-related factors in fluids, such as human blood. More specifically, this invention pertains to improvements in cartridges of the type wherein gas flows through a fluid sample in a reaction chamber of the cartridge to create bubbles of fluid for the purpose of detecting and analyzing coagulation, coagulation time, and other and coagulation-related factors.

Examples of gas flow cartridges and gas flow techniques for detecting and analyzing coagulation and coagulation-related factors are disclosed in the aforementioned application and in U.S. Pat. Nos. 4,000,972 and 4,074,971, all assigned to the assignee of the present invention. In general, these gas flow cartridges are characterized by a vertically oriented enclosure or tube-like member which has a reaction chamber located therein above a reagent chamber. The reagent chamber contains various additives or reagents which are mixed with the fluid to be tested in the reaction chamber. The reagent chamber is loaded with reagent at the time when the cartridge is manufactured. The reaction chamber is loaded with the fluid sample to be tested at the time of the test. An actuator mechanism operable in conjunction with the cartridge collapses the reagent chamber and forces its contents into the reaction chamber. Gas is injected into the reaction chamber and flows upward through its contents. Bubbles of fluid are formed and coagulation is detected by detecting coagulation of the fluid which forms the bubbles.

In the aforesaid application Ser. No. 434,718, the gas flow cartridge employs resilient sealing plug members positioned at the upper and lower ends of the reagent chamber. These resilient members each include a dome portion having slits formed therethrough. The resiliency of the material normally holds the slit in a closed position to seal the liquid reagent within the reagent chamber from the time of manufacture until it is ultimately used some period of time later. It has been determined, however, that to obtain the best fluid tight closure of the slit in the dome member, the slit must be formed at a relatively precise length. Variations in the length of the slit and in other construction dimensions of the dome portion and in the resiliency of the material of the dome portion can result in leaks of reagent from the reagent chamber prior to use of the cartridge. Although coating the surfaces of the dome portion at the closed slit with low shear strength sealant reduces the possibilities of leaks, the coating technqiue has not proved universally successful in terminating leaks under all conditions. A reduction in the amount of reagent in the reagent chamber due to leakage prior to the analytical test can alter the test results under some conditions.

Slits formed smaller than the optimum size or length are too restrictive to the gas flow. An excessive back-pressure develops and flow of gas through the contents of the reaction chamber is reduced. Variable effects on coagulation are created and, as a result, statistical reliability in detecting coagulation can be affected.

Slits which are larger and smaller than the critical size also have a corresponding effect on the size of bubbles created. Variations in bubble size also introduce variables which may have an effect on the consistent detection of coagulation.

The hydrostatic pressure necessary to force open the slit of the resilient dome portion can also cause reagent leaks around the nozzle which injects the gas into the reaction chamber. This pressure is caused by the resiliency of the dome portion when the slit is held open by the gas pressure flowing through the slit.

These factors, among others, underly the improvements of the present invention.

SUMMARY OF THE INVENTION

In accordance with its broad aspects, the gas flow cartridge of the present invention includes an elongated pin member which is movably retained within a communication opening of a separating structure which separates the reagent and reaction chambers. The separating structure includes a resilient member through which the communication opening extends. A first portion of the pin member has an operative configuration for sealing the communication opening when the first portion is positioned in the communication opening. A second portion of the pin member, which is longitudinally displaced from the first portion, has an operative configuration for opening the communication opening to fluid communication therethrough upon longitudinal movement of the pin member to a position where the second portion is within the communication opening. Preferably, the second portion of the pin member includes at least one longitudinally extending groove indented into the pin member through which the fluid flows when the groove is located in the communication opening. The cartridge is initially assembled with the first portion of the pin member located within the communication opening. The resilient member circumjacently surrounds and presses against the first portion and establishes the fluid-tight seal. This seal is a reliable and is not distrubed until the cartridge is used. Upon longitudinal movement of the pin member, which occurs when the cartridge is used in the coagulation-related analytical test, the second portion is moved into the communication opening to establish a communication path between the reagent and reaction chambers. The groove in the second portion of the pin member defines a direct communication path of consistent cross sectional area which does not create variable back pressures or bubble sizes.

In accordance with still other aspects of the present invention, the lower plug member at the bottom of the reagent chamber includes a resilient membrane which is adapted to contact the lower end of the pin member and to move the pin member upward as the lower plug member is moved upward. The plug member is moved upward to force the reagent in the reagent chamber through the communication opening and into the reaction chamber. The grooved second portion of the pin member moves into the communication opening to create the communication path soon after the lower plug starts its upward movement. Consequently, very little increase in hydrostatic pressure occurs within the reaction chamber before the communication path is opened. The membrane is initially integral non-pervious material of the lower plug member. A sharp needle on the actuator mechanism pierces the member for the purpose of injecting gas into the cartridge as the lower plug member is moved upward. The needle pierces the membrane after the communication path has been opened so there is no undesirable pressure build-up which would tend to force reagent from the reagent chamber into the needle. Once the lower plug member has been moved upward and the reagent is within the reaction chamber, gas is delivered from the needle and flows through the opened communication opening into the reaction chamber.

The nature and details of the present invention can be more completely understood by reference to the following description of a preferred embodiment, taken in conjunction with the drawings, and from the appended claims.

DRAWINGS

DETAILED DESCRIPTION

Figures 1, 2:
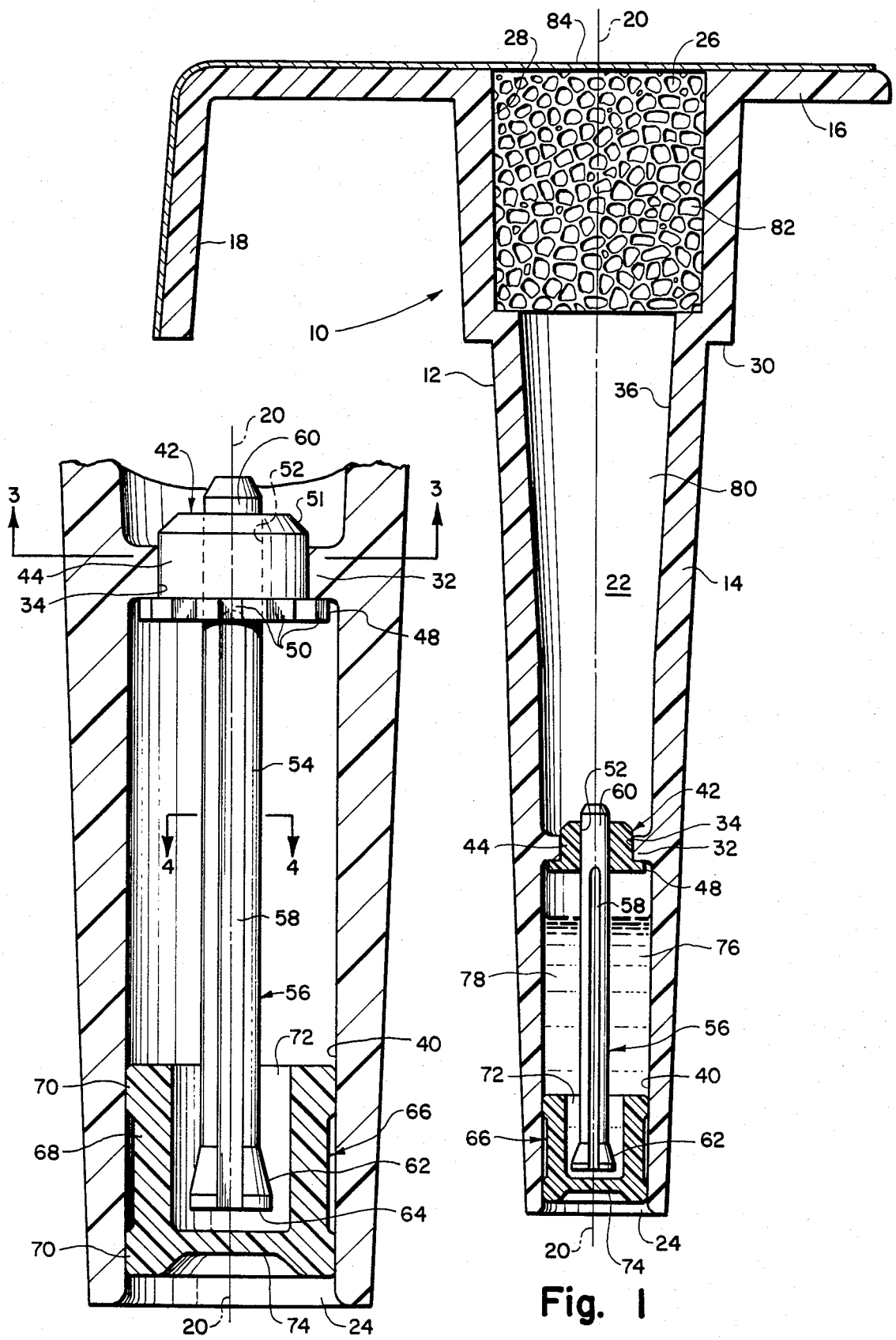
FIG. 1 is a vertical section view taken axially through a test cell of a gas flow cartridge in accordance with the present invention.
FIG. 2 is an enlarged portion of FIG. 1 illustrating details of a disc member, a guide pin member, and a lower plug member of the cartridge.

The presently preferred embodiment of the gas flow cartridge of the present invention is shown in FIGS. 1 and 2. The gas flow cartridge, referenced 10 herein, includes a housing 12 preferably formed of integral clear acrylic plastic. A plurality (preferably four, although only one is shown) of transversely spaced and vertically oriented tube-like members 14 extend downward from an upper shelf portion 16 of the housing 12. A lip 18 extends downward from a forward edge of the shelf portion 16. Each of the tube-like members 14 has essentially the same predetermined configuration, and its shape is concentric about a center axis 20 through each tube-like member 14. Details of the nature and use of the housing 12, shelf portion 16 and lip 18 are more fully described in the aforesaid application Ser. No. 434,718, incorporated herein by reference.

Each tube-like member 14 defines an enclosure for a test cell 22. Each tube-like member 14 has an open interior which terminates at an open lower end 24 and an open upper end 26. The upper end 26 is integrally connected to the shelf portion 16. An initial upper portion of the tube-like member extends downward from the upper end 26 and defines an interior, generally cylindrical surface 28. The extent along the axis 20 to which the cylindrical surface 28 extends is approximately the same as the distance which the lip 18 extends downward from the forward edge of the upper shelf portion 16. An annular shoulder 30 extends radially inward at the lower end of the cylindrical surface 28. A partition 32 extends radially inward toward the axis 20 at a position intermediate the shoulder 30 and the lower end 24. A cylindrical passageway 34 extends axially through the partition 32. A downwardly-converging, frustoconical-shaped inner surface 36 extends from the shoulder 30 to a position intermediate the shoulder 30 and the partition 32. A substantially cylindrical surface 38 extends from the lower end of the frustoconical-shaped surface 36 to the partition 32. Another cylindrical surface 40 extends downward from the partition 32. The lower edge of the cylindrical surface 40 is divergently curved radially outward at the lower end 24 of the tube-like member.

A disc member 42, which is formed of resilient, flexible material such as Kraton, is frictionally retained within the axial passageway 34 of the partition 32. The disc member 42 includes a generally cylindrical main body portion 44. A radially outer circumferential surface of the main body portion 44 is resiliently seated within the passageway 34 and presses against the partition 32 to provide a fluid-tight seal therebetween. An annular flange 48 extends radially outward from the lower end of the main body portion 44 and contacts the lower surface of the partition 32. The flange 48 may be of a continuous disc configuration (not shown) or may be formed with rectangular openings 50 extending axially therethrough (as is shown in FIG. 2). An inwardly converging upper beveled end 52 of the main body portion 44 facilitates insertion of the disc member 42 into the passageway 34. The disc member 42 defines a radially-centered, axially-extending and cylindrically-shaped communication opening 52 extending therethrough. It is through the communication opening 52 that fluid communication occurs, as is discussed below.

A shank 54 of a guide pin 56 is received within the communication opening 52 of the disc member 54. The shank 54 presents a generally uniform diameter cylindrical outside surface along its full length, except for a pair of axially extending and radially indented grooves 58 formed therein. The upper ends of the grooves 58 are located below the upper end of the shank 54, thereby leaving an upper first portion 60 of the shank 54 which presents a uniformly smooth cylindrical outer surface. The grooves extend longitudinally along a second portion of the shank.

Figure 3:
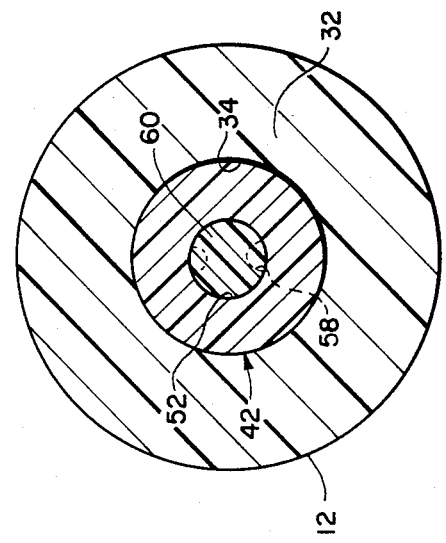
FIG. 3 is a section view taken substantially in the plane of line 3—3 of FIG. 2.

When initially assembled, the outer cylindrical surface of the upper portion 60 is located and retained within the communication opening 52 in the disc member, as shown in FIGS. 1 and 2. The diameter of the upper portion 60 is slightly larger than the diameter of the communication opening 52 when the opening is unoccupied. When the shank uupper portion 60 is inserted in the opening 52, the resilient material of the main body portion 44 circumjacently surrounds and presses against the upper portion 60, as shown in FIG. 3, to establish a fluid-tight sealing relationship between the upper cylindrical portion 60 and the main body portion 44 at the center opening 52. Upon upward movement of the guide pin 56 relative to the disc member 42 from the position illustrated in FIG. 2, the grooves 58 extend axially through and above and below the disc member communication opening 52. A fluid communication path is thereby established within the grooves through the communication opening 52.

Figure 4:
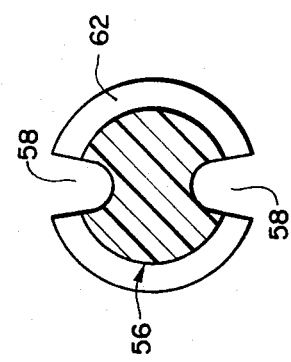
FIG. 4 is a section view taken substantially in the plane of line 4—4 of FIG. 2.

The lower end of the guide pin 56 includes an outwardly-diverging flared lower portion 62. The grooves 58 extend axially through the lower flared portion 62, as shown in FIG. 4. The flared portion 62 is of greater transverse width than the shank portion 54 to prevent the guide pin 56 from moving upward through the communication opening 52. A bottom surface 64 of the flared portion 62 extends generally perpendicularly with respect to the axis 20 about which the guide pin 56 is centered. The bottom surface 64 can be flat or formed slightly concavely upward into the flared portion 62. The bottom surface 64 provides an enlarged surface area greater than the cross sectional area of the shank 54, and the surface 64 acts as means upon which to contact the guide pin 56 and to move or slide it upward.

A lower plug member 66, which is also formed of resilient, flexible material such as Kraton, is frictionally retained against the lower cylindrical surface 40 of the tube member 14. The lower plug member 66 exhibits rotational concentricity about the center axis 20. The plug member 66 includes a generally cylindrical center body portion 68, from which a pair of ring-like edges 70 protrude outwardly at each axial end of the plug member 66, as is best shown in FIG. 2. The edges 70 frictionally engage with and resiliently press and seal against the surface 40 of the tube member 14. A center cylindrical opening 72 extends downwardly into the center body portion 68. An integral membrane 74 of the plug member 66 extends across the lower axial end of the center body portion 68 and closes the center opening 72 at its lower end. The membrane 74 is an integral continuous portion of the plug member 66 and is initially non-pervious in that it contains no openings, slits or other means for fluid communication therethrough.

In assembling the aforementioned elements of the cartridge 10, the guide pin 56 is inserted into the communication opening 52 of the disc member 42 until the upper cylindrical surface 60 is positioned within the cylindrical opening 52 to thereby seal the communication opening 52. Thereafter, the guide pin 56-disc member 42 assembly is inserted upward from the lower end 24 of the tube-like member 14 until the disc member is retained within the passageway 34 of the partition 32. The plug member 66 is inserted also from the lower end 24 until the edges 70 frictionally engage with and resiliently press and seal against the surface 40. When positioned in the assembled relationship shown in FIGS. 1 and 2, the membrane 74 is spaced slightly below the bottom surface 64 of the guide pin 56.

Before the plug member 66 is inserted, a predetermined quantity and type of reagent 76 is inserted into a reagent chamber 78. The reagent chamber 78 is enclosed and defined at the upper end by the disc member 42, at the sides by the surface 40, and at the lower end by the plug member 66. The reagent 76 is confined within the reagent chamber 78 by the sealing relationships between the disc member body portion 44 and the partition passageway 34, and between the cylindrical guide pin upper portion 60 and the communication opening 52, and between the plug member 66 and the tube surface 40. To insert the reagent 76 into the reagent chamber 78, the housing 12 is inverted from the position shown in FIGS. 1 and 2, and the reagent 76 is added into the reagent chamber 78. A wire or other similar device is placed alongside the edges 70 of the plug member 66 as it is inserted into the lower tube end 24. Thereafter the wire is withdrawn. The wire deforms the edges 70 to vent air from the reagent chamber 78 as the plug member 66 moves into the reagent chamber during assembly.

The type and quantity of reagent 76 inserted into the reagent chamber 78 depends on the purpose for which the cartridge 10 is to be used. For dose response tests on blood samples, heparin will typically be part of the reagent. A different quantity of heparin will be introduced into the reagent chambers 78 of each of the test cells 22 in a single cartridge 10. For titration tests on blood samples, the reagent could include heparin or protamine, in variable amounts in each of the reagent chambers of the test cells. For clotting time tests on blood samples, the same predetermined quantity of activating substance is introduced into each of the reagent chambers in each of the test cells 22.

An upper reaction chamber 80 is defined on the sides by the surfaces 36 and 38 and extends axially above the disc member 42 to the shoulder 30. The partition 32 and disc member 42 are thus seen to serve as a structure or means for separating the upper reaction chamber 80 from the lower reagent chamber 78. An open-cell foam member 82 is inserted from the upper end 26 into the upper interior opening within the cylindrical surface 28. The foam member 82 is preferably of a right cylindrical configuration, and its axial length is approximately the same as the distance from the shoulder 30 to the upper end 26. The foam member 82 is inserted downwardly until it contacts the shoudler 30, and the lower edge of the foam member extends across the upper margin of the reaction chamber 80. Prior to insertion, the foam member 82 and its internal structure is coated with a debubbling agent such as silicone. The debubbling agent causes liquid contacting the strand-like or fiber-like internal structure of the foam member 82 to reflux or drain away and not collect in the interstices in the foam material, but the debubbling agent is ineffective to prevent coagulated fluid from accumulating in the interstices of the foam material. Preferably, the material of the foam member 82 is formed of synthetic plastic, such as polyurethane.

A cover 84 is attached to the upper surface of the shelf portion 16 and lip 18. The cover 84 is preferably a single piece of paper and is attached preferably by an adhesive backing. The paper cover 84 contains printed indicia and a code (not shown) indicative of the type of analytical test to be conducted with the cartridge. The type of test is determined by the type and quantity of reagent 76 present in each reagent chamber 78 of the cartridge. Furthermore, printed indicia may also indicate the quantities or strengths of reagent in the reagent chambers. The code may be machine-readable as is discussed more fully in the aforesaid patent application Ser. No. 434,718. A sample of fluid to be tested is inserted into the reaction chamber 80 by piercing the cover 84 and foam member 82 with a syringe needle and injecting the sample from the syringe into the reaction chamber.

The cartridge 10 is used in conjunction with a machine having an actuator mechanism which operatively forces the reagent 76 from the reagent chamber 78 into the reaction chamber 80, delivers a flow of gas upward through the mixed fluid sample and reagent within the reaction chamber to create bubbles, optically or otherwise senses the coagulation state or condition of the fluid sample by sensing coagulated fluid of the bubbles, and measures or otherwise keeps track of the elapsed time and/or analytical conditions associated with the event of coagulation. The machine and the actuator assembly are described in greater detail in the aforesaid patent application Ser. No. 434,718, whose disclosure is incorporated herein by reference.

For purposes of a present understanding, the actuator mechanism is referenced 85 in FIGS. 5 to 8 and includes a nozzle member 86 which is reciprocatively moved vertically during the course of the analytical test, a sharpened needle 88 at the top center of the nozzle member 86 which operatively pierces the membrane 74 of the lower plug member 66 and delivers the flow of gas into the test cell 22, a receptacle 90 for holding each tube-like member 14 and the cartridge 10, a top cover assembly 92 which is movable outward to cover the top of the cartridge 10 and maintain it within the receptacle 90 during the test, a coagulation detection sensor 94 positioned to receive and sense radiation or light transmitted through the foam member 82 from a radiation or light source 95 and thereby provide a signal indicative of the event of coagulation when the coagulated fluid of the bubbles accumulates in the foam member, and a cartridge sensor 96 positioned within the top cover assembly 92 also receptive of the radiation or light from source 95 for providing signals indicative of the type of cartridge and analytical test to be performed.

Figure 5:
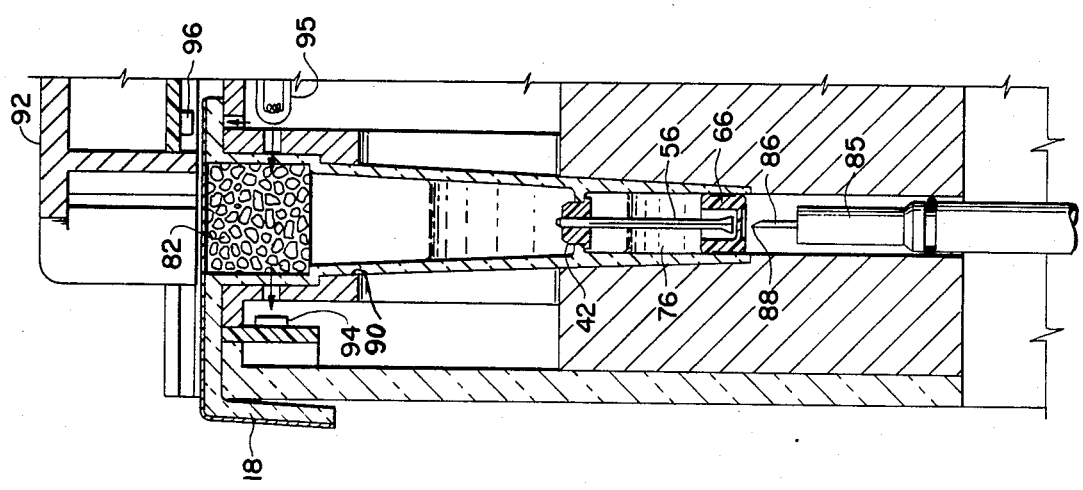

A coagulation-related analytical test commences by inserting the cartridge 10 into the actuator mechanism 85 and moving the top cover assembly 92 forward, as illustrated in FIG. 5. The nozzle member 86 and the needle 88 are spaced below and do not contact the lower plug member 66 when the cartridge is first inserted into the actuator mechanism.

Figure 6:
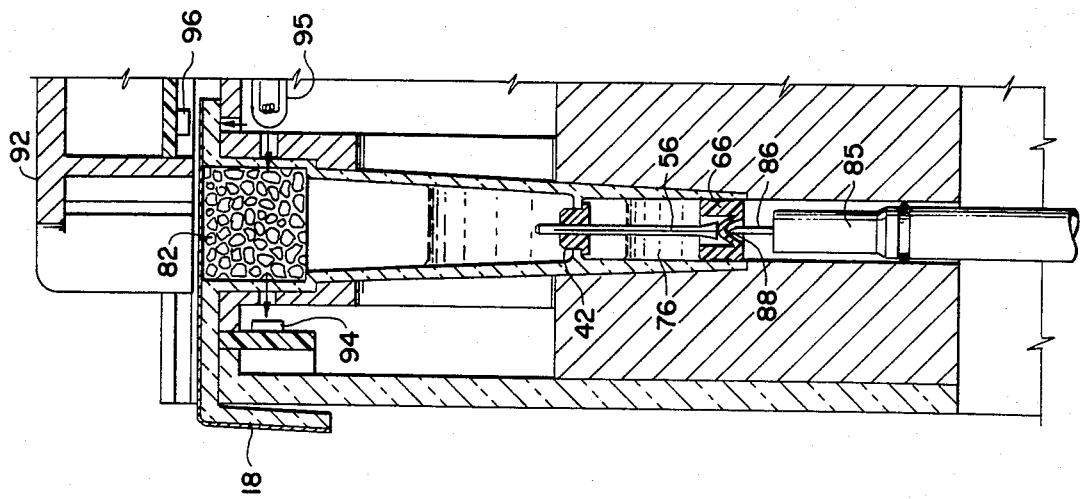
FIGS. 5, 6, 7, 8 and 9 are vertical section views of one test cell of the gas flow cartridge shown in FIG. 1 within an actuator mechanism and illustrating in sequence the use of the cartridge in a coagulation detection analytical test.

Thereafter, the nozzle member 86 moves upward and an upper pointed edge of the needle 88 contacts the membrane 74, as shown in FIG. 6. The membrane 74 deforms upward in a cone-like manner. The membrane contacts the bottom surface 64 of the guide pin 56. Continued upward movement of the nozzle member 86 continues to deform the membrane 74 and pushes the guide pin 56 upward. The shank 54 begins sliding through the communication opening 52 of the disc member 42. The membrane 74 continues deforming upward until the upper cylindrical surface 60 of the guide pin 54 moves out of the communication opening 52 and the grooves 58 extend through the center opening 52. At this point, the communication path is established within the grooves 58 through the opening 58 between the reagent chamber 78 and the reaction chamber 80.

The resiliency of the material from which the membrane 74 and plug member 66 is constructed is sufficient to open the reagent chamber 78 to communication with the reaction chamber 80 prior to the sharpened edge of the needle 88 piercing the membrane 74. Because of the relatively slight upward deformation of the membrane 74 prior to movement of the grooves 58 through the communication opening 52, a relatively small increase in hydrostatic pressure occurs within the reagent chamber prior to opening the reagent chamber to the reaction chamber. The relatively low increase in hydrostatic pressure does not force any of the reagent 76 out of the reagent chamber.

Continued upward movement of the nozzle member 86 causes the needle 88 to pierce the membrane 74 after the communication path to the reaction chamber 80 has been opened by the grooves 58. Once the communication path to the reaction chamber 80 is opened, atmospheric pressure exists within both the reaction and reagent chambers. As the needle 88 pierces the membrane 74, there is no pressure build-up in the reagent chamber which would cause the reagent to squirt or be expelled downward into the needle 88.

Figure 7:
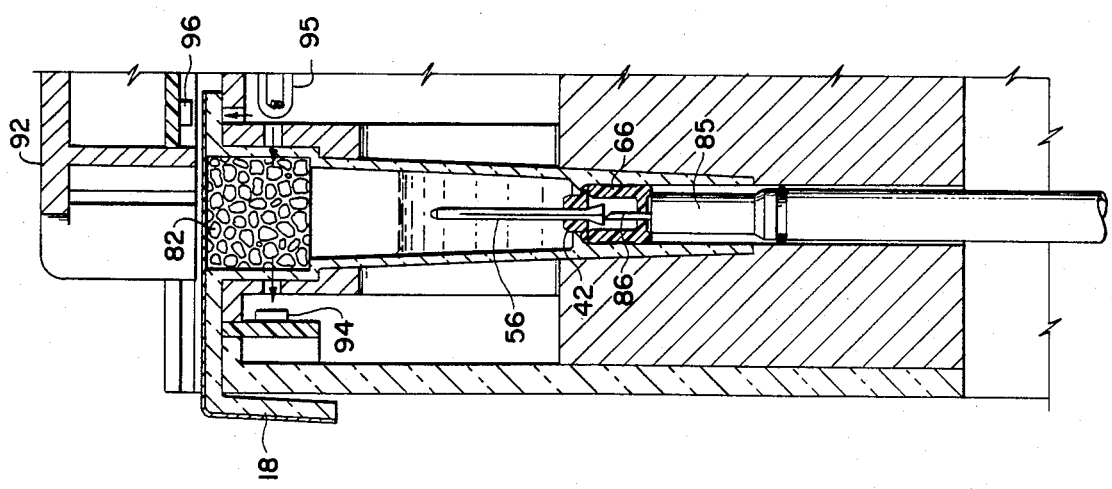

The nozzle member 86 continues to move upward after the needle 88 pierces the membrane 74 and contacts and pushes the plug member 66 upward to a position where it is adjacent the partition 32, as shown in FIG. 7. The reagent chamber 78 is collapsed, and the reagent 76 is forced through the grooves 58 and into the reaction chamber 80, where it is mixed with the blood or other fluid sample which is subjected to the coagulation-related analytical test. The guide pin 56 moves upward with the plug member 66. The relatively wide flat bottom surface 64 of the lower flared portion 62 of the guide pin provides an enlarged contact surface for the point of the needle 88 to contact as the nozzle member 86 moves upward. The flared portion 62 contacts the disc main body portion 44 and prevents the guide pin from floating upward into the reagent chamber. Since the grooves 58 extend through the lower flared portion 62 (FIG. 4), a communication path continues to exist into the reaction chamber 80.

Figure 9:
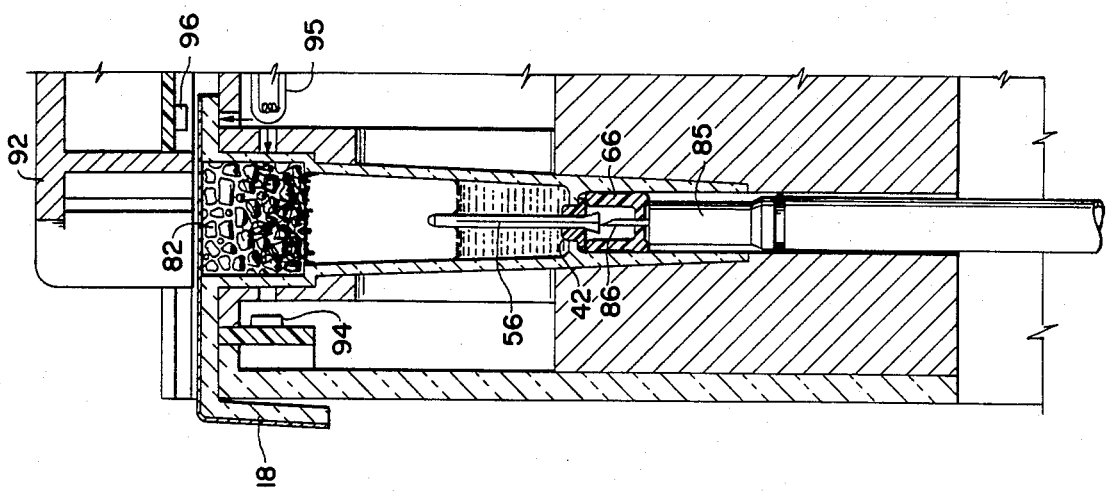
Figure 8:
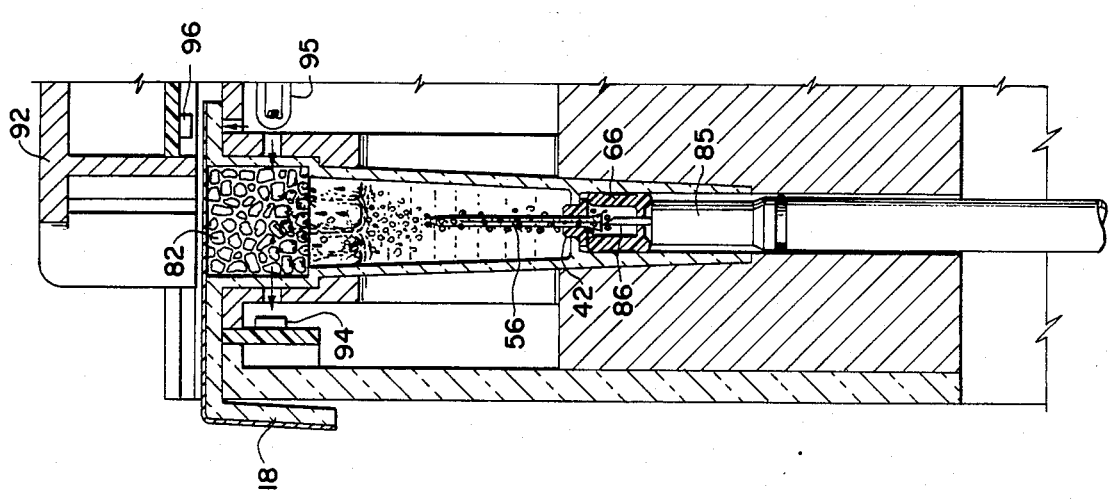

Gas is next conducted upward through the needle 88 of the nozzle member 86 and flows into the reaction chamber 80, as shown in FIG. 8. The angled pointed upper edge of the needle 88 allows gas to escape between the upper edge of the needle 88 and the bottom surface 64 of the guide pin. The gas flows upward in the grooves 58 through the disc communication opening 52. The gas flow initially mixes the reagent with the pool of fluid in the bottom of the reaction chamber by agitating the fluid. After a short mixing period, the analytical test commences. The gas flow lifts bubbles of fluid above the surface of the pool of fluid in the reaction chamber. The bubbles rise up to the foam member 82. The debubbling agent on the foam member collapses the bubbles and refluxes or drains the liquid of the bubbles back into the pool at the bottom of the reaction chamber. This process continues until coagulation commences, at which time the debubbling agent of the foam member 82 is ineffective on coagulated fluid. The coagulated fluid of the bubbles collects in the foam member 82 and the collected coagulated fluid obscures or obstructs the light transmission path through the foam member sensed by the coagulation detection sensor 94, as shown in FIG. 9. The coagulation detection sensor 94 signals the event of coagulation. The coagulation analytical test is terminated and the gas flow is stopped. The cartridge 10 is thereafter removed from the actuator mechanism 85.

Substantially improved gas flow through the pool of fluid in the reaction chamber and uniformity in the size of the bubbles lifted up to the foam member results from the direct open communication path from the end of the needle 88 into the reaction chamber. The direct open communication path is provided by the grooves 58 within the disc communication opening 52. In contrast to the use of slits in a resiliently deformable member as disclosed in the aforementioned patent application Ser. No. 434,718, no substantial back pressure occurs. A more uniform predictable gas flow results from the direct open communication path available from the present invention. The size of the bubbles is more consistent because the flow rate is more predictable. With uniform sized bubbles, the amount of fluid carried by each bubble is more predictable and the rate of accumulation of coagulated fluid in the foam member 82 is more uniform, all resulting in more statistically reliable test results.

Another improvement over the aforementioned slits is that all of the seals provided in the present gas flow cartridge are reliable, consistent seals. Of course, the integral membrane 74 has no opening therethrough until it has been pierced when the cartridge is used. The resilient pressure of the disc main body portion 44 against the upper cylindrical surface 60 of the guide pin shank portion 54 secures a reliable sealing arrangement which is not disturbed until the guide pin 56 is moved upward upon use. Accordingly, there is a substantially reduced possibility for leakage of the reagent 76 from the reagent chamber prior to use of the cartridge.

The described arrangement of the present invention also avoids the necessity to break away certain plastic portions of the tube-like member 14, as has been typical in prior arrangements illustrated by the aforesaid U.S. Pat. Nos. 4,000,972 and 4,074,971, assigned to the assignee hereof. Other advantages and improvements are also inherent from the structure and arrangement of the gas flow cartridge 10 of the present invention.

The nature and operation of the present invention has been shown and described with a degree of specificity. It should be understood, however, that the specificity of the description has been made by way of preferred example, and that the invention is defined by the scope of the appended claims.

What is claimed is:

1. In a cartridge in which to conduct a coagulation-related test on fluid, having a reaction chamber into which the fluid is inserted for the test and also having a reagent chamber containing reagent to be mixed with the fluid in the reaction chamber at the time of the test by transferring the reagent from the reagent chamber to the reaction chamber at the commencement of the test, an improved means for sealing the reagent in the reagent chamber prior to the test and for opening the reagent chamber and reaction chamber for communication of the reagent therebetween at the commencement of the test, comprising in combination:
    separating means for separating the reagent and reaction chambers and for defining a communication opening therethrough between the chambers, and
    an elongated pin member longitudinally movably retained within the communication opening, and having a first portion initially positioned within the communication opening and of an operative configuration for sealing the communication opening when positioned therein, and also having a second portion longitudinally displaced along the pin member from the first portion and of an operative configuration for opening the communication opening to fluid communication therethrough upon longitudinal movement of said pin member positioning the first portion out of the communication opening at the commencement of the test.

2. A cartridge as recited in claim 1 wherein the second portion of the pin member includes at least one groove-like indention extending longitudinally along said pin member through which fluid is communicated through the communication opening.

3. A cartridge as recited in claim 1 wherein said separating means includes a resilient member through which the communication opening extends and which resiliently presses circumjacently against the first portion of the pin member when the first portion is within the communication opening.

4. A cartridge as recited in claim 3 wherein the second portion of the pin member includes at least one groove-like indention extending longitudinally along said pin member through which fluid is communicated through the communication opening.

5. A cartridge as recited in claim 4 of the type wherein the reagent chamber is defined at least in part by a movable resilient plug member adapted to be moved longitudinally within the cartridge toward said separating means to force the reagent from the reagent chamber into the reaction chamber, and wherein said cartridge is utilized with an actuator mechanism including nozzle means for moving the plug member to force the reagent into the reaction chamber and for injecting gas through the plug member into the fluid and reagent contained within the reaction chamber, and wherein said improvement further comprises:
    an integral and initially non-pervious membrane of said plug member adapted to be moved upward to contact and longitudinally move the pin member and thereafter to be pierced by said nozzle means.

6. A cartridge as recited in claim 5 wherein said membrane possesses resilient characteristics to deform sufficiently during upward movement of said nozzle means to result in piercing of said membrane not substantially earlier than the opening of the communication opening to fluid communication therethrough.

7. A cartridge in which to conduct a coagulation-related test on fluid, comprising:
    a tube-like member having an open interior extending longitudinally therethrough from a lower end to an upper end;
    separating means within the tube-like member for separating the open interior into a lower chamber and an upper chamber, said separating means defining a communication opening therethrough between the upper and lower chambers;
    an elongated pin member longitudinally movably retained within the communication opening, and having a first portion of an operative configuration for sealing the communication opening when positioned therein, and also having a second portion longitudinally displaced along the pin member from the first portion and having an operative configuration for opening the communication opening for fluid communication therethrough when the second portion is moved into the communication opening; and
    means associated with the elongated pin member for contacting and moving the elongated pin member from a first position wherein the first portion of the pin member is in the communication opening to a second position wherein the second portion of the pin member is within the communication opening.

8. A cartridge as recited in claim 7 wherein said separating means further comprises a resilient member circumjacent of and defining the communication opening, said resilient member resiliently pressing against the operative configuration of the first portion of the pin member when the pin member is in the first position to operatively seal the upper and lower chambers against fluid communication therebetween.

9. A cartridge as recited in claim 8 wherein said separating means further comprises:
    a partition of the tube-like member located within the open interior at a position intermediate the upper and lower ends of the tube-like member, said partition including a passageway formed therethrough; and said resilient member is resiliently frictionally retained within the passageway to allow the pin member to move longitudinally relative thereto, and said resilient member defines the communication opening therethrough.

10. A cartridge as recited in claim 9 wherein the second portion of the pin member is defined by at least one indented groove extending generally longitudinally of the pin member a sufficient distance to provide fluid communication within the groove through the communication opening when the pin member is in the second position.

11. A cartridge as recited in claim 7 further comprising:
a plug member operatively sealing the open interior of the lower chamber and initially operatively positioned adjacent the lower end of the tube-like member, said plug member including a resilient membrane extending generally transversely across the open interior of the lower chamber; and wherein
said pin member extends into the lower chamber and terminates at a bottom surface spaced above the membrane when the pin member is in the first position; and
said plug member is adapted to be moved upward in the lower chamber to a position adjacent said separating means, and said membrane adapted to contact the bottom surface of said pin member during movement of the pin member from the first position to the second position.

12. A cartridge as recited in claim 11 wherein:
said pin member includes a lower portion having a substantially greater transverse width than the second portion of the pin member, the lower portion defining the bottom surface extending transversely of the pin member, the bottom surface having an area substantially greater than the cross sectional areas of either of the first and second portions of the pin member;
the second portion of the pin member is longitudinally spaced below the first portion and above the lower portion;
the second portion of the pin member is defined by at least one indented groove extending generally longitudinally of the pin member a sufficient distance to provide fluid communication within the groove through the communication opening when the pin member is in the second position; and
the indented groove extends substantially downwardly from the second portion through the lower portion of the pin member.

13. A cartridge as recited in claim 12 wherein said cartridge is of the type for flowing gas through the open interior of the tube-like member during the coagulation-related test on the fluid, and wherein:
the membrane of the lower plug member is adapted to be pierced by a needle through which gas is supplied to said cartridge.

14. A cartridge in which to conduct a coagulation-related test on fluid by flowing gas through the fluid during the test, comprising:
a tube-like member having an open interior extending longitudinally therethrough from a lower end to an upper end;
separating means within the tube-like member for separating the open interior into a lower chamber and an upper chamber, said separating means defining a communication opening therethrough between the upper and lower chambers;
a plug member retained within and operatively sealing the open interior of the lower chamber, said plug member including a resilient membrane operably extending transversely across the open interior within the lower chamber and upwardly movable toward said separating means; and
an elongated pin member operatively retained within the open interior to be moved generally longitudinally therein and relative to said separating means, said pin member including a first portion operatively contacting and sealing against said separating means at the communication opening when the pin member is in a first position in which the first portion is within the communication opening, said pin member also having a second portion defining a communication path through the communication opening when said pin member is in a second position in which the second portion is within the communication opening, said pin member also including contact means extending into the lower chamber at a position relative to the membrane of said plug member to be contacted during upward movement of the membrane, the continued upward movement of the membrane after contact with the contact means operatively moving the pin member from the first position to the second position.

15. A cartridge as recited in claim 14 wherein the plug member is operatively movable within the interior of the lower chamber from the lower end of the tube-like member toward said separating means, and the membrane is adapted to be pierced by a needle means through which gas is injected into the open interior.

16. A cartridge as recited in claim 15 wherein said separating means comprises:
a partition of the tube-like member extending transversely into the open interior between the upper and lower chambers, said partition defining a passageway extending therethrough; and
a resilient member positioned within the passageway of the partition, the resilient member circumjacently defining the communication opening, the resilient member resiliently circumjacently pressing against the first portion of the pin member when the pin member is in the first position, the resilient member operatively retaining the pin member within the open interior and allowing longitudinal movement of the pin member relative to the resilient member.

17. A cartridge as recited in claim 16 wherein the second portion of the pin member includes at least one indented groove extending generally longitudinally of the pin member through which the communication path through the communication opening is defined when the pin member is in the second position.

18. A cartridge in which to conduct a coagulation-related test by passing gas through a sample of fluid inserted therein, comprising:
a tube-like member having an interior surface and defining an open interior extending generally along an axis therethrough from a lower end to an upper end;
a partition located within the open interior of the tube-like member and extending inward toward the axis at a position intermediate the upper and lower ends of the tube-like member, said partition generally separating the open interior into a lower chamber between the partition and the lower end and into an upper chamber between the partition and the upper end, the partition further defining a passageway therethrough between the upper and lower chambers;

a resilient member operatively resiliently retained within and sealing against the passageway of the partition, said resilient member further defining a communication opening therethrough between the upper and lower chambers, the resilient member circumjacently surrounding the communication opening;

a plug member initially positioned adjacent the lower end of the tube-like member operatively extending across and sealing against the interior surface of the tube-like member within the lower chamber, said plug member adapted to be axially moved along the interior surface of the lower chamber toward the partition and the resilient member, said plug member including a center body portion centered generally with respect to the axis within the lower chamber and at least one edge extending outward from the main body portion and contacting the interior surface of the tube-like member in the lower chamber, the center body portion defining a center opening extending axially into the center body portion from an upper end of the plug member, said plug member also including an integral membrane extending across the closing the center opening at the lower end of the center body portion;

an elongated pin member axially movably retained within the communication opening of the resilient member, said elongated pin member having a first portion near an upper end thereof initially positioned within the communication opening and of an operative configuration for sealing the communication opening when positioned therein, said pin member also having a lower portion at the opposite end of the pin member from the first portion and extending into the lower chamber and terminating at a position spaced above the membrane of said plug member, said pin member further having a second portion longitudinally spaced therealong below the first portion and above the lower portion, the second portion being of an operative configuration for opening the communication opening to fluid communication therethrough upon longitudinal movement of the pin member wherein the second portion is within the communication opening;

a predetermined quantity and type of fluid reagent initially confined within the lower chamber;

a foam member coated with debubbling agent operatively retained at the upper chamber adjacent the upper end of the tube-like member; and wherein upward movement of the plug member contacts the membrane with the lower portion of the pin member and axially moves the pin member to the position where the second portion of the pin member is within the communication opening.

19. A cartridge as recited in claim 18 wherein the second portion of the pin member is defined by at least one groove indented into the pin member and extending generally longitudinally thereof a sufficient distance to provide fluid communication through the groove between the upper and lower chambers when the second portion is positioned within the communication opening.

20. A cartridge as recited in claim 19 wherein the membrane of the plug member is adapted to be pierced by a needle-like member through which gas is injected into the open interior of the tube-like member.

21. A cartridge as recited in claim 20 wherein the lower portion of the pin member includes a bottom surface extending transversely thereacross and of transverse width substantially greater than the transverse width of the pin member at the first and second portions, the bottom surface of the lower portion being adapted to be contacted by the needle-like member after piercing the membrane.

22. A cartridge as recited in claim 21 wherein the groove extends longitudinally from the second portion through the lower portion to the bottom surface of the pin member.

* * * * *